United States Patent
Andrus et al.

(10) Patent No.: US 10,202,410 B2
(45) Date of Patent: Feb. 12, 2019

(54) SCAPHOPETALONE ANALOGS AND THEIR USES

(71) Applicant: Brigham Young University, Provo, UT (US)

(72) Inventors: Merritt B. Andrus, Lindon, UT (US); F. Brent Johnson, Orem, UT (US); Mary Ruth Jaeger Greer, Seal Beach, CA (US); Rex G. Cates, Orem, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 15/282,468

(22) Filed: Sep. 30, 2016

(65) Prior Publication Data

US 2017/0152280 A1 Jun. 1, 2017

Related U.S. Application Data

(60) Provisional application No. 62/236,753, filed on Oct. 2, 2015.

(51) Int. Cl.
| | |
|---|---|
| *C07C 59/68* | (2006.01) |
| *C07H 15/207* | (2006.01) |
| *C07D 307/88* | (2006.01) |
| *C07D 307/92* | (2006.01) |
| *C07D 317/48* | (2006.01) |
| *C07D 407/12* | (2006.01) |
| *C07H 15/203* | (2006.01) |

(52) U.S. Cl.
CPC ............ *C07H 15/207* (2013.01); *C07C 59/68* (2013.01); *C07D 307/88* (2013.01); *C07D 307/92* (2013.01); *C07D 317/48* (2013.01); *C07D 407/12* (2013.01); *C07H 15/203* (2013.01)

(58) Field of Classification Search
None
See application file for complete search history.

(56) References Cited

PUBLICATIONS

Fürer, Planta Med 2016; 82: 930-941.*
Entry for beta-apoplicatitoxin, https://www.chemicalbook.com/ChemicalProductProperty_EN_CB32301166.htm, downloaded from the internet Dec. 19, 2017.*
Entry for rooperol, http://www.chemspider.com/Chemical-Structure.4943425.html, downloaded from the internet Dec. 19, 2017.*
Stevenson, Journal of Natural Products vol. 54, No. 1, pp. 310-314, Jan.-Feb. 1991.*
Klemm, J. Org. Chem., vol. 37, No. 12, 1972.*
Zhao, J. Nat. Prod. 2006, 69, 1145-1152.*
Ye, Zhongcaoyao (2013), 44 (19), 2642-2646.*
Vecchietti, Phytochemistry, 1979, vol. 18, pp. 1847-1849.*
Vardamides, Phytochemistry 62 (2003) 647-650.*
Daugan, Journal of Natural Products, vol. 54, No. 1, pp. 110-118, Jan.-Feb. 1991.*
Carlucci, M., et al., "Antiherpetic activity and mode of action of natural carrageenans of diverse structural types," *Antiviral Research*, 43:93-102 (1999).
Chattopadjyay, D., et al., "Ethnomedicines for the development of anti-herpesvirus agents," D. Chattopadhyay (ed), In: *Ethnomedicine: A Source of Complementary Therapeutics*, pp. 117-147 (2010). ISBN: 978-81-308-0390-6.
Chayavichitslip, P., et al., "Herpes simplex," *Pediatrics Review*, 30:119-129 (2009).
Jaeger Greer, Mary R., et al., Activity of acetone and methanol extracts from thirty-one medicinal plant species against herpes simplex virus types 1 and 2, *Pharmaceutical Biology*, 48(9):1031-1037 (2010).
Klemm, L.H., et al., "Intramolecular Diels-Alder Reactions. 10. Synthesis and Cyclizations of Some N-(Cinnamyl and phenylpropargyl)cinnamamides and Phenylpropiolamides," *J. Organic Chemistry*, 41:2571-2579 (1976).
Looker, K.J., et al., "An estimate of the global prevalence and incidence of herpes simplex virus type 2 infection," *Bulletin of the World Health Organization*, 86:805-812 (2008).
Ojewole, J., "Antihypertensive Properties of Bryophyllum Pinnatum {(LAM) OKEN} Leaf Extracts," *American Journal of Hypertension, Ltd.*, 15:A34-A239 (2002).
Xu, F., et al., "Trends in Herpes Simplex Virus Type 1 and Type 2 Seroprevalence in the United States," *Journal of the American Medical Association*, 296:964-973 (2006).
Adjanohoun, E.A.M., et al., "Traditional Medicine and Pharmacopoeia: Contributions to ethnobotanical and floristic studies in western Nigeria," *Organization of African Unity Press* (1991). pp. 318 and 337.

* cited by examiner

*Primary Examiner* — Layla D Berry

(74) *Attorney, Agent, or Firm* — Brinks Gilson & Lione; Ryan L. Marshall; Jonathan M. Hartley

(57) ABSTRACT

The present disclosure relates to scaphopetalone analogs, methods of making the analogs, and their uses.

2 Claims, 3 Drawing Sheets

SCAPHOPETALONE ANALOGS AND THEIR USES

REFERENCE TO EARLIER FILED APPLICATION

This application claims the benefit under 35 U.S.C. § 119(e) of U.S. Provisional Patent Application No. 62/236,753, filed Oct. 2, 2015, and titled "Scaphopetalone Analogs and Their Uses," which is incorporated, in its entirety, by this reference.

TECHNICAL FIELD

The present disclosure relates to scaphopetalone analogs, methods of making the analogs, and their uses.

BACKGROUND

*Kalanchoe pinnata* Linn (Crassulaceae) is an herbaceous perennial 30-120 cm in height that likely originated in Madagascar. It is widely used as an ornamental and reproduces primarily by producing plantlets in the notches of its leaf margins. It is often labeled as an invasive species due to this prolific reproduction and it now abounds around dwellings, along roadsides, and in abandoned farms in tropical regions. *K. pinnata* is used as an herbal remedy for an array of human disorders including hypertension, diabetes mellitus, bruises, wounds, boils, abscesses, insect bites, arthritis, rheumatism, headaches, ulcers, diarrhea, and as a painkiller. It produces a host of secondary metabolites including alkaloids (analgesic/antibacterial effects), terpene-based saponins (stop bleeding), flavonoids (antioxidant properties), and tannins (healing wounds and some antiviral activity).

BRIEF SUMMARY

In one aspect, a compound of formula (I) is provided:

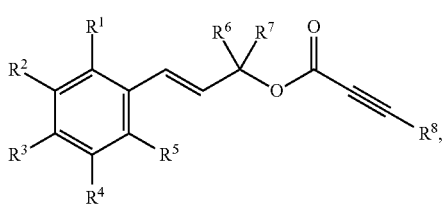

(I)

where $R^1$, $R^2$, $R^3$, $R^4$ and $R^5$ are each independently selected from the group consisting of hydrogen, halogen, —OH, —CF$_3$, C$_{1-10}$ alkyl, C$_{1-10}$ alkoxy, aryl, —O-aryl, heteroaryl, and —O— heteroaryl; $R^6$ and $R^7$ are each independently selected from the group consisting of hydrogen, halogen, C$_{1-10}$ alkyl, and C$_{1-10}$ alkoxy; and $R^8$ is selected from the group consisting of substituted or unsubstituted aryl, heteroaryl, or C$_{5-10}$ cycloalkyl.

In another aspect, a compound of formula (II), or a pharmaceutically acceptable salt or optical isomer thereof, is provided:

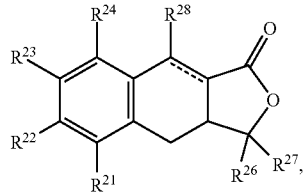

(II)

where $R^{21}$, $R^{22}$, $R^{23}$, and $R^{24}$ are each independently selected from the group consisting of hydrogen, halogen, —OH, —CF$_3$, C$_{1-10}$ alkyl, C$_{1-10}$ alkoxy, aryl, —O-aryl, heteroaryl, and —O— heteroaryl; $R^{26}$ and $R^{27}$ are each independently selected from the group consisting of hydrogen, halogen, C$_{1-10}$ alkyl, and C$_{1-10}$ alkoxy; $R^{28}$ is selected from the group consisting of substituted or unsubstituted aryl, heteroaryl, or C$_{5-10}$ cycloalkyl; and ═══ represents a single or double bond.

In yet another aspect, a compound of formula (III), a pharmaceutically acceptable salt or optical isomer thereof, is provided:

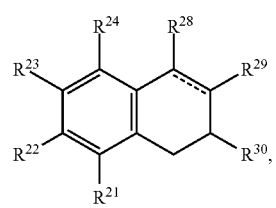

(III)

where $R^{21}$, $R^{22}$, $R^{23}$, and $R^{24}$ are each independently selected from the group consisting of hydrogen, halogen, —OH, —CF$_3$, C$_{1-10}$ alkyl, C$_{1-10}$ alkoxy, aryl, —O-aryl, heteroaryl, and —O— heteroaryl; $R^{28}$ is substituted or unsubstituted aryl, heteroaryl, or C$_{5-10}$ cycloalkyl; $R^{29}$ and $R^{30}$ are each independently —(C═O)R$^{30'}$ or —R$^{30'}$OR$^{30'}$, each R$^{30'}$ is independently selected from the group consisting of H, C$_{1-10}$ alkyl, C$_{1-10}$ alkoxy, aryl, heteroaryl, —COOH, a hydrogen bond donor, a hydrogen bond acceptor and a sugar; and ═══ represents a single or double bond, provided that the compound is not

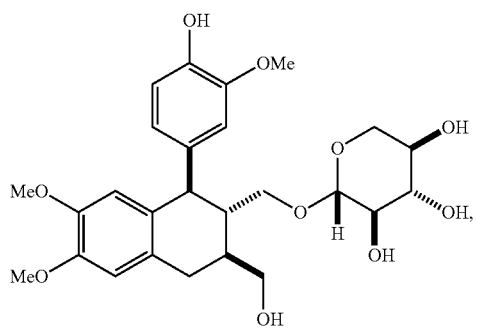

-continued

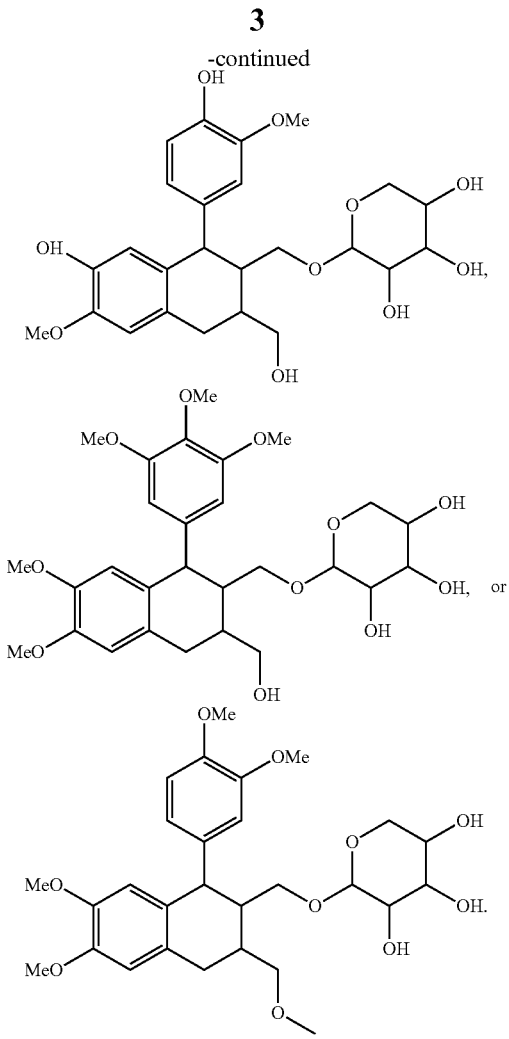

In still another aspect, a pharmaceutical composition comprising any compound, pharmaceutically acceptable salt or optical isomer of this disclosure is provided. In a further aspect, a method comprises administering a pharmaceutically effective amount of a compound, pharmaceutically acceptable salt or optical isomer of this disclosure to a patient in need thereof. In yet another aspect, a method for treating a viral disease in a patient comprises administering a pharmaceutically effective amount of a compound, pharmaceutically acceptable salt or optical isomer of this disclosure to a patient having a viral disease. In further another aspect, a method for preparing a compound comprises forming an intramolecular Diels-Alder product using the compound of formula (I) above as a starting material.

In another aspect, a method for preparing a compound comprises reducing a compound of formula (IVa)

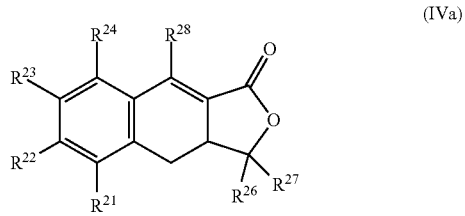

(IVa)

to a compound of formula (IVb)

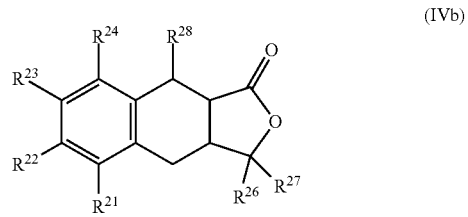

(IVb)

where $R^{21}$, $R^{22}$, $R^{23}$, and $R^{24}$ are each independently selected form the group consisting of hydrogen, halogen, —OH, $C_{1-10}$ alkyl, $C_{1-10}$ alkoxy, aryl, —O-aryl, heteroaryl, and —O-heteroaryl; $R^{26}$ and $R^{27}$ are each independently selected from the group consisting of hydrogen, halogen, $C_{1-10}$ alkyl, and $C_{1-10}$ alkoxy; and $R^{28}$ is selected from the group consisting of substituted or unsubstituted aryl, heteroaryl, or $C_{5-10}$ cycloalkyl.

In yet another aspect, a method for preparing a compound comprises reducing a compound of formula (Va)

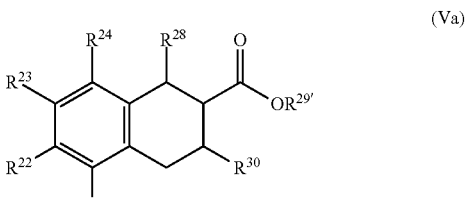

(Va)

to a compound of formula (Vb)

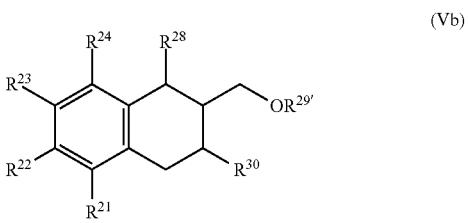

(Vb)

wherein $R^{21}$, $R^{22}$, $R^{23}$, and $R^{24}$ are each independently selected form the group consisting of hydrogen, halogen, —OH, $C_{1-10}$ alkyl, $C_{1-10}$ alkoxy, aryl, —O-aryl, heteroaryl, and —O-heteroaryl; $R^{28}$ is substituted or unsubstituted aryl, heteroaryl, or $C_{5-10}$ cycloalkyl; $R^{29}$ is hydrogen, or a sugar; and $R^{30'}$ is —OH, $C_{1-10}$ alkoxy, —COOH, a hydrogen bond donor or a hydrogen bond acceptor.

DETAILED DESCRIPTION

Figure 1A:
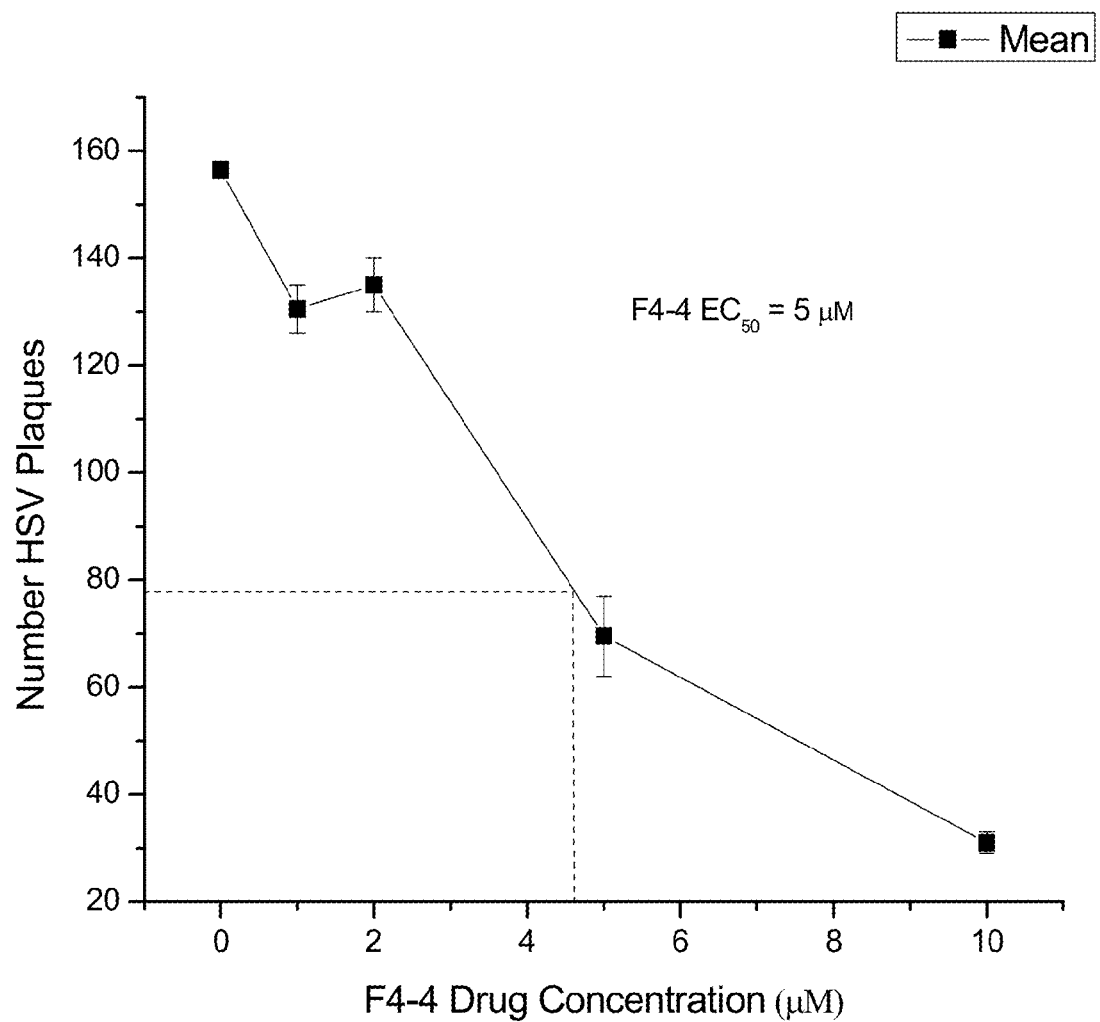
FIG. 1A and FIG. 1B illustrate the determination of median effective concentration ($EC_{50}$) of antiviral activity in fraction F4-4 (FIG. 1A) and F4-0 (FIG. 1B) against Herpes simplex Type 2 virus. The assay was performed in C1008 cells, and miniplaques were visualized after immunoperoxidase staining.

Diseases caused by the herpes viruses are significant in the human population even though estimating the global needs is difficult due to poor availability of data. Even so, HSV-1 and HSV-2 have worldwide rates of infection of between 65% and 90%, are generally higher in females than males at ages over 14 years, infections increase with age, neonatal infections are often serious, and these viruses cause mild to severe lifelong infections and morbidity. Few drugs are available for treating diseases caused by these pathogens, and there is an unmet need to discover novel anti-herpes drugs.

The leaves of the *Kalanchoe pinnata* Linn (Crassulaceae) plant have anti-HSV-2 activity. Applicant discovered that an acetone extract from the roots had much greater anti-herpes activity, and the mechanism of this activity involved a significant reduction in the activity of five key viral genes. The present disclosure provides fractionation of this extract using high pressure liquid chromatography, testing fractions against herpes viruses, and eventual identification through 2D NMR and other techniques to identify two active, temperature-stable, scaphopetalone compounds F4-0 and F4-4 from *K. pinnata*. The structures of these compounds were characterized in NMR studies. These compounds are highly active against Herpes simplex viruses 1 (HSV-1) and 2 (HSV-2) and Herpes zostera (>5 µM). These viruses pose significant health challenges causing diseases such as cold sores, sexually-transmitted diseases, and shingles.

The present disclosure further provides methods of making the scaphopetalone compounds F4-0 and F4-4 that are produced in very small amounts (1-2 mg) in the roots of *K. pinnata* Linn (Crassulaceae), their analogs and intermediates, and their uses.

The details of the disclosure are set forth in the accompanying description below. Although methods and materials similar or equivalent to those described herein can be used in the practice or testing of the present disclosure, illustrative methods and materials are now described. Other features, objects, and advantages of this disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

Unless otherwise specifically defined, "heteroaryl" means a monovalent monocyclic aromatic radical of 5 to 10 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein.

In one embodiment, a compound of formula (I) is provided:

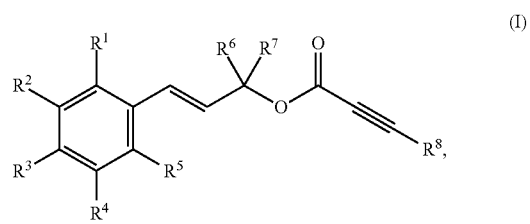

wherein $R^1$, $R^2$, $R^3$, $R^4$ and $R^5$ are each independently selected from the group consisting of hydrogen, halogen, —OH, —CF$_3$, C$_{1-10}$ alkyl, C$_{1-10}$ alkoxy, aryl, —O-aryl, heteroaryl, and —O— heteroaryl;

$R^6$ and $R^7$ are each independently selected from the group consisting of hydrogen, halogen, C$_{1-10}$ alkyl, and C$_{1-10}$ alkoxy; and $R^8$ is selected from the group consisting of substituted or unsubstituted aryl, heteroaryl, or C$_{5-10}$ cycloalkyl.

Preferably, $R^1$, $R^4$ and $R^5$ are hydrogen. Preferably, $R^2$ and $R^3$ are each independently halogen, —OH, C$_{1-10}$ alkoxy, —O-aryl, or —O-heteroaryl. More preferably, $R^2$ and $R^3$ are halogen, —OH, or C$_{1-10}$ alkoxy, and $R^1$, $R^4$ and $R^5$ are hydrogen.

Preferably, $R^6$ or $R^7$ is hydrogen. More preferably, both $R^6$ and $R^7$ are hydrogen. Preferably, $R^8$ is aryl or heteroaryl. More preferably, $R^8$ is phenyl, unsubstituted or substituted with one or more of halogen, —OH, —CF$_3$, C$_{1-10}$ alkyl, C$_{1-10}$ alkoxy, aryl, —O-aryl, heteroaryl, and —O-heteroaryl.

In one embodiment, $R^8$ is

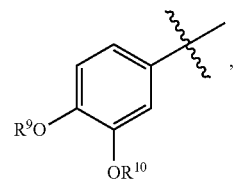

wherein $R^9$ and $R^{10}$ are each independently hydrogen, C$_{1-10}$ alkyl, aryl, or heteroaryl. Preferably, $R^8$ is

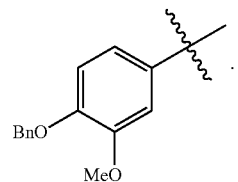 [SMILES: *c1ccc(OCc2ccccc2)c(OC)c1]

In one embodiment, the compound of formula (I) is

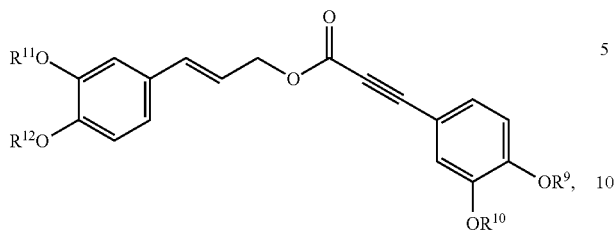

wherein $R^9$, $R^{10}$, $R^{11}$ and $R^{12}$ are each independently hydrogen, $C_{1-10}$ alkyl, aryl, or heteroaryl.

In one embodiment, the compound of formula (I) is

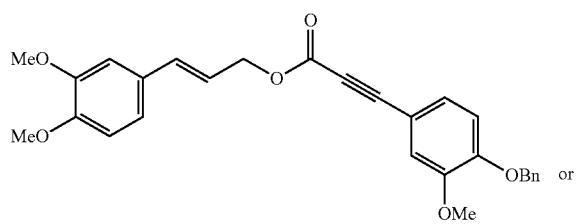

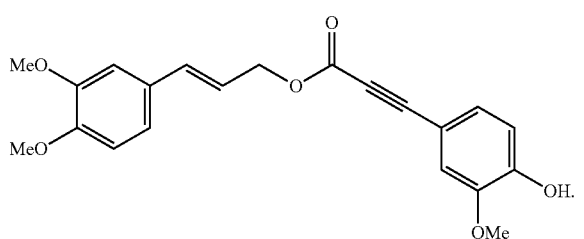

In one embodiment, a compound of formula (II), or a pharmaceutically acceptable salt or optical isomer thereof is provided:

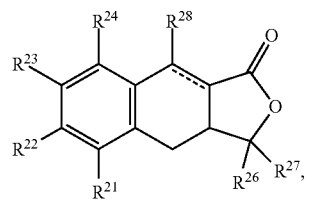

wherein $R^{21}$, $R^{22}$, $R^{23}$, and $R^{24}$ are each independently selected from the group consisting of hydrogen, halogen, —OH, —CF$_3$, $C_{1-10}$ alkyl, $C_{1-10}$ alkoxy, aryl, —O-aryl, heteroaryl, and —O— heteroaryl;

$R^{26}$ and $R^{27}$ are each independently selected from the group consisting of hydrogen, halogen, $C_{1-10}$ alkyl, and $C_{1-10}$ alkoxy;

$R^{28}$ is selected from the group consisting of substituted or unsubstituted aryl, heteroaryl, or $C_{5-10}$ cycloalkyl; and $=\!=\!=$ represents a single or double bond.

Preferably, $R^{21}$ and $R^{24}$ are hydrogen. Preferably, $R^{22}$ and $R^{23}$ are each independently halogen, —OH, $C_{1-10}$ alkoxy, —O-aryl, or —O-heteroaryl. More preferably, $R^{22}$ and $R^{23}$ are halogen, —OH, or $C_{1-10}$ alkoxy, and $R^{21}$ and $R^{24}$ are hydrogen.

In one embodiment, $R^{26}$ or $R^{27}$ is hydrogen. Preferably, both $R^{26}$ and $R^{27}$ are hydrogen. Preferably, $R^{28}$ is aryl or heteroaryl. More preferably, $R^{28}$ is phenyl, unsubstituted or substituted with one or more of halogen, —OH, —CF$_3$, $C_{1-10}$ alkyl, $C_{1-10}$ alkoxy, aryl, —O-aryl, heteroaryl, and —O-heteroaryl.

In another embodiment, $R^{28}$ is

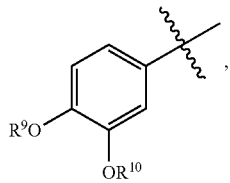

wherein $R^9$ and $R^{10}$ are each independently hydrogen, $C_{1-10}$ alkyl, aryl, or heteroaryl. Preferably, $R^{28}$ is

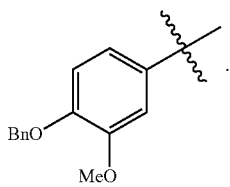 [SMILES: *c1ccc(OCc2ccccc2)c(OC)c1]

In another embodiment, compounds of formula (II) are provided

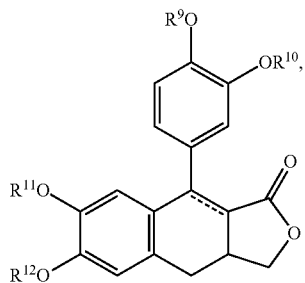

wherein $R^9$, $R^{10}$, $R^{11}$ and $R^{12}$ are each independently hydrogen, $C_{1-10}$ alkyl, aryl, or heteroaryl.

Preferably, the compound of formula (II) is

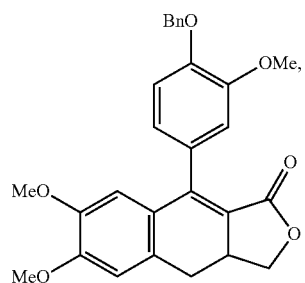

-continued

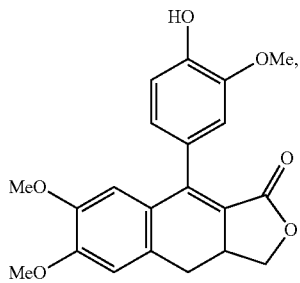

In another embodiment, compounds of formula (III), a pharmaceutically acceptable salt or optical isomer thereof are provided:

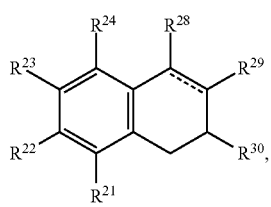
(III)

wherein $R^{21}$, $R^{22}$, $R^{23}$, and $R^{24}$ are each independently selected from the group consisting of hydrogen, halogen, —OH, —CF$_3$, C$_{1-10}$ alkyl, C$_{1-10}$ alkoxy, aryl, —O-aryl, heteroaryl, and —O— heteroaryl;

$R^{28}$ is substituted or unsubstituted aryl, heteroaryl, or C$_{5-10}$ cycloalkyl;

$R^{29}$ and $R^{30}$ are each independently —(C=O)R$^{30}$ or —R$^{30}$OR$^{30}$, each $R^{30}$ is independently selected from the group consisting of H, C$_{1-10}$ alkyl, C$_{1-10}$ alkoxy, aryl, heteroaryl, —COOH, a hydrogen bond donor, a hydrogen bond acceptor and a sugar; and ═══ represents a single or double bond,
provided that the compound is not

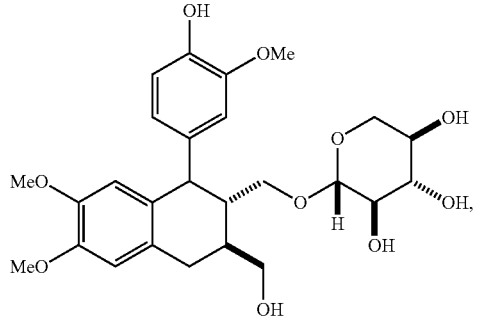

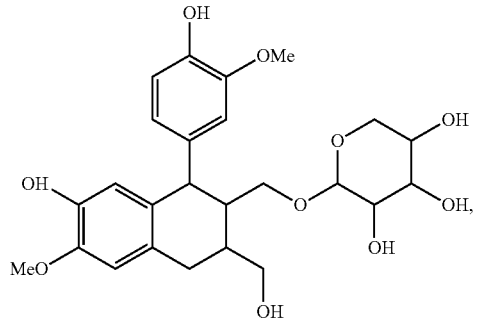

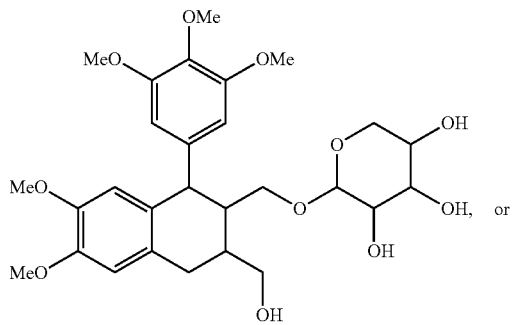

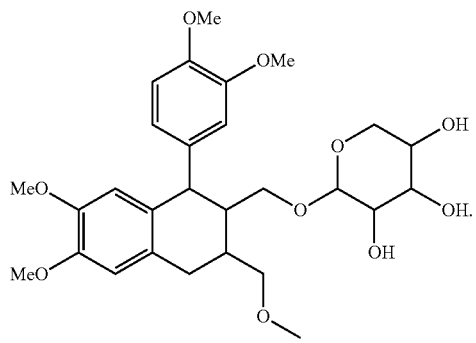

Preferably, $R^{21}$ and $R^{24}$ are hydrogen. More preferably, $R^{22}$ and $R^{23}$ are each independently halogen, —OH, C$_{1-10}$ alkoxy, —O-aryl, or —O-heteroaryl. Preferably, $R^{22}$ and $R^{23}$ are halogen, —OH, or C$_{1-10}$ alkoxy, and $R^{21}$ and $R^{24}$ are hydrogen.

In one embodiment, $R^{28}$ is aryl or heteroaryl. Preferably, $R^{28}$ is phenyl, unsubstituted or substituted with one or more of halogen, —OH, —CF$_3$, C$_{1-10}$ alkyl, C$_{1-10}$ alkoxy, aryl, —O-aryl, heteroaryl, and —O-heteroaryl.

In one embodiment, $R^{28}$ is

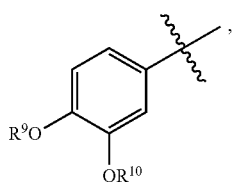

wherein $R^9$ and $R^{10}$ are each independently hydrogen, $C_{1-10}$ alkyl, aryl, or heteroaryl.

In one embodiment, a compound of formula (III) is further defined as a compound of formula (IV)

(IV)

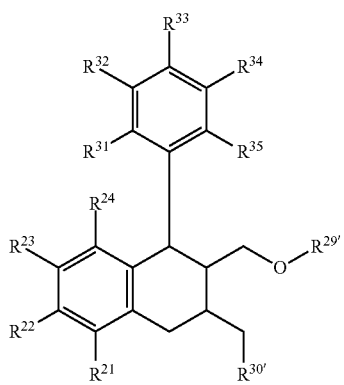

wherein $R^{29'}$ is hydrogen or a sugar, wherein $R^{30'}$ is —OH, $C_{1-10}$ alkoxy, —COOH, a hydrogen bond donor or a hydrogen bond acceptor, and wherein $R^{31}$, $R^{32}$, $R^{33}$, $R^{34}$ and $R^{35}$ are each independently selected from the group consisting of hydrogen, —OH, halogen, $C_{1-10}$ alkyl, $C_{1-10}$ alkoxy, —$CF_3$, —$SO_3$, aryl, —O-aryl, heteroaryl, and —O-heteroaryl.

In one embodiment, a compound of formula (IV) is of formula (V)

(V)

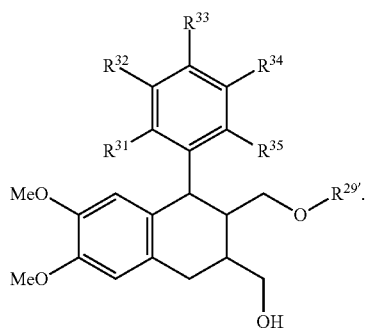

In one embodiment, the compound of formula (III) is

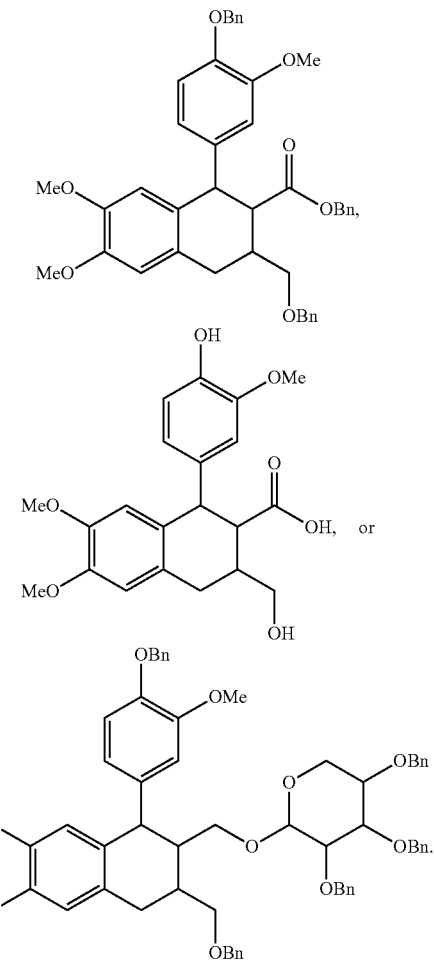

In one embodiment, a pharmaceutical composition is provided comprising any of the compounds, pharmaceutically acceptable salts or optical isomers thereof disclosed in the present disclosure, such as compounds, pharmaceutically acceptable salts or optical isomers of formulae (I), (II) or (III).

In one embodiment, a method comprises administering a pharmaceutically effective amount of the compound, pharmaceutically acceptable salt or optical isomer thereof disclosed in the present disclosure, such as compounds, pharmaceutically acceptable salts or optical isomers of formulae (I), (II) or (III) to a patient in need thereof.

In one embodiment, a method for treating a viral disease in a patient comprises administering a pharmaceutically effective amount of the compound, pharmaceutically acceptable salt or optical isomer thereof disclosed in the present disclosure, such as compounds, pharmaceutically acceptable salts or optical isomers of formulae (I), (II) or (III) to a patient having a viral disease.

The viral disease may be caused by a Herpes virus, such as a Herpes simplex virus 1, a Herpes simplex virus 2, or a Herpes zostera virus. The viral disease may be cold sore, genital herpes, or shingles caused by a Herpes virus.

Extracted Compounds

Figure 1B:
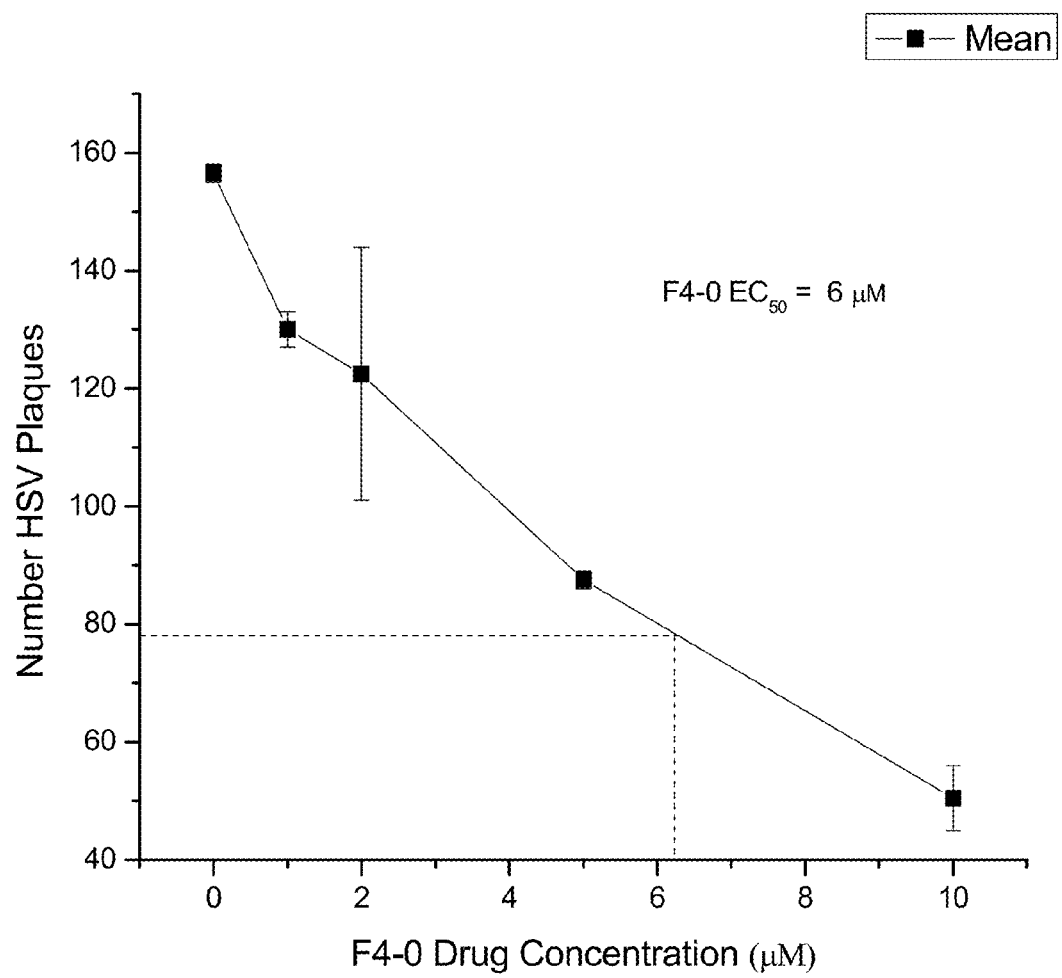
Figure 2:
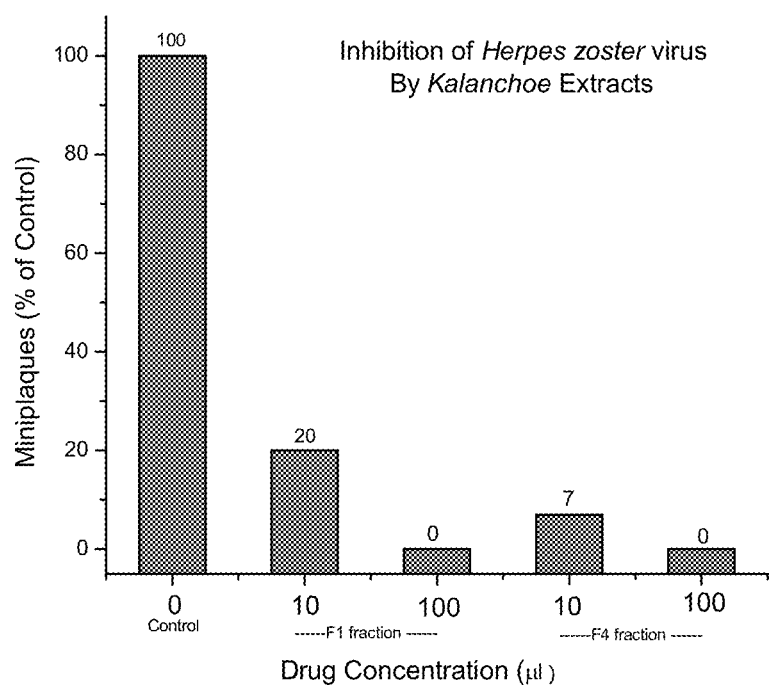
FIG. 2 illustrates inhibition of Herpes Zoster virus by components in fractions 1 and 4. Virus-induced miniplaques were assessed in shell vial culture by immunofluorescence.

Bioassays of the extract and purified, natural compounds (HPLC, 1-2 mg) against HSV-1, HSV-2, and *H. zostera* indicate significant activity of extracts and/or drugs from four natural populations as well as greenhouse grown plants against HSV (FIG. 1A and FIG. 1B for F4-0, F4-4) and *H. zostera* (FIG. 2 of *H. zostera*). In addition, the mechanism of action of the compounds in the active fraction of the extract is to disrupt the function of viral DNA. The in vitro activity of HSV-1 and HSV-2 viral RNA transcripts produced from five viral genes (alpha gene UL54, beta genes UL23 and UL30, and gamma genes US4 and UL17) were reduced anywhere from 55 to nearly 500 fold by the addition of the KOH, gave 3 on multi gram scale (75%, 5 g). Esterification with cinnamic alcohol 4 has provided the intermediate ester 5. An intramolecular vinyl-benzene Diels-Alder reaction, performed under thermal conditions, provided the bicyclic lactone 6 (80%). Alternatively, this intramolecular vinyl-benzene Diels-Alder reaction can be performed in the presence of a AgF catalyst or a chiral catalyst such as the AgX•chiral ligand catalyst (X=Br or Cl).

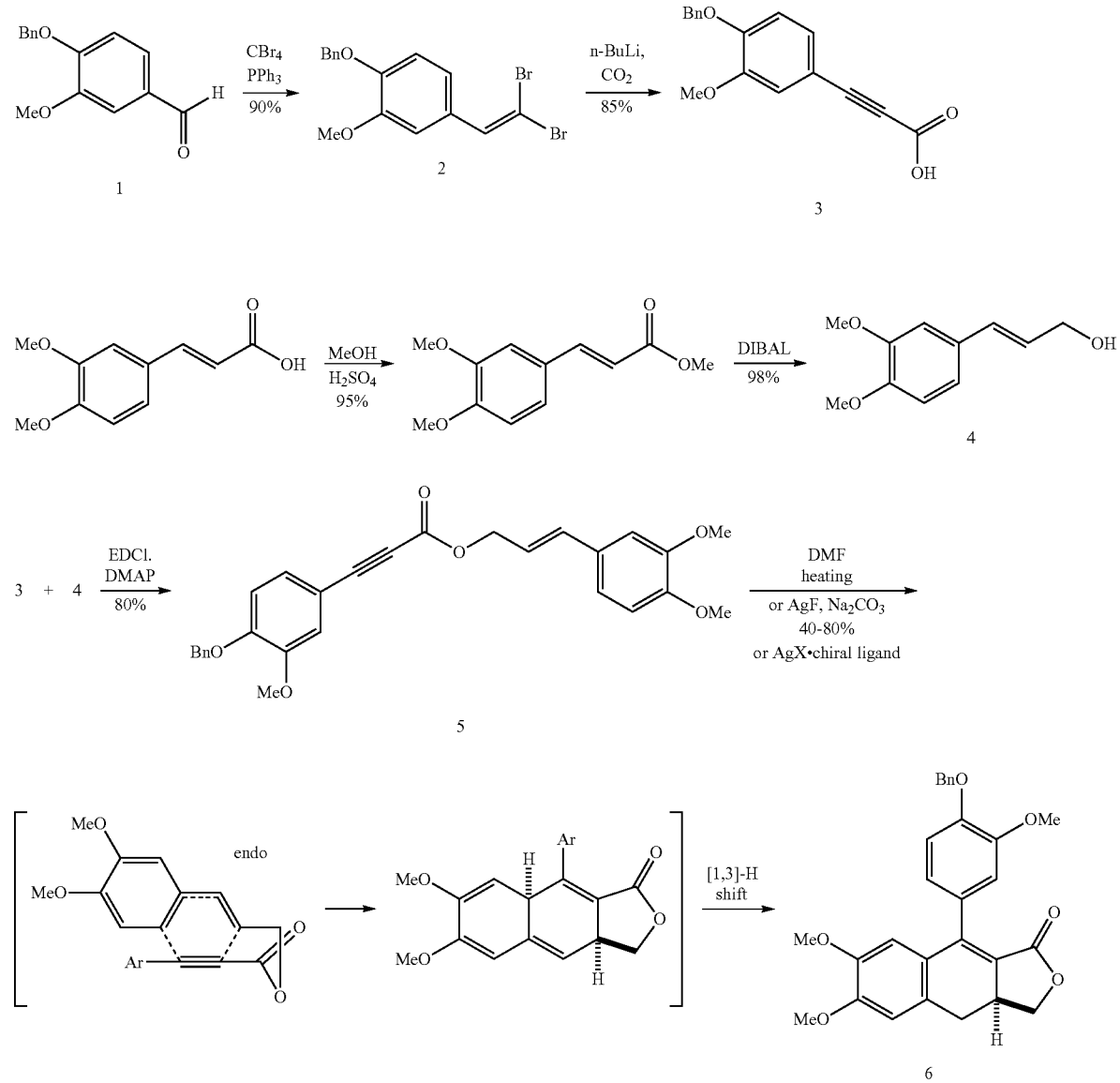

*K. pinnata* extract with little detectable cytotoxicity to the host cells. These data suggested that gram quantities of synthesized intermediates and compounds were needed for future studies.

Synthesis of Analog Compounds

The potent compound F4-4 is a new, unique member of the scaphopetalone class of lignin-derived, natural products. As shown in Scheme 1, the synthesis of F4-4 began with inexpensive benzyl protected vanillin 1. Cinnamate ester formation (95%), bromination, and treatment with base, As shown in Scheme 2, reduction of 6 with magnesium turnings in methanol will provide 7 with the needed anti-anti stereochemistry shown. Opening the lactone will give benzyl ester 8 and reduction with DIBAL will allow for attachment of the needed benzyl protected xylose sugar 9 (X=Cl or Br) to access intermediate 10. Removal of the benzyl ether protecting groups under standard hydrogenation conditions with catalytic Pd/C will then give the desired target, F4-4.

Scheme 2, Synthesis of Scaphopetalone And Its Analogs

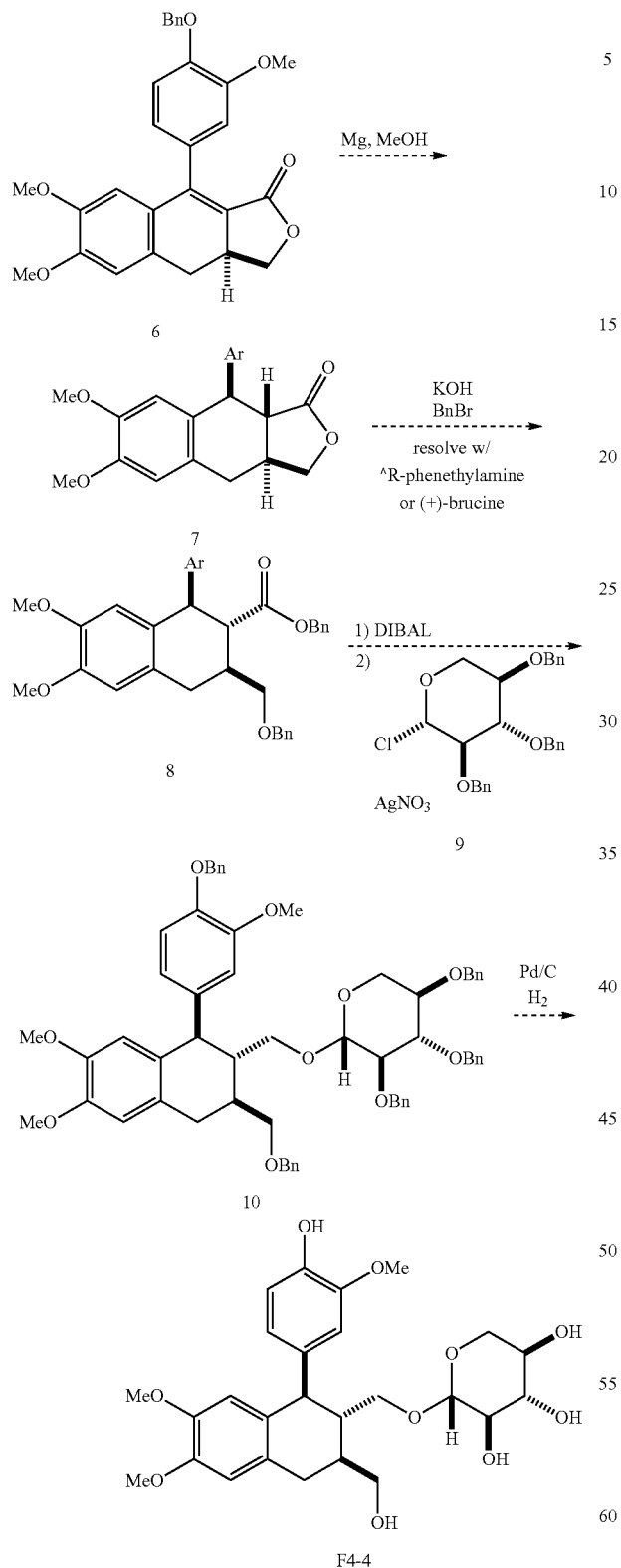

The synthesis of F4-0, the benzoyl glucoside, is more straightforward and followed the route in the preparation of F4-4. F4-4 analogs, with various substituents on the F4-4 aryl rings and suitable sugars, can be synthesized in similar routes. These synthetic routes will allow for multigram production of the various scaphopetalone compounds, their intermediates and analogs, which will allow for critical animal studies needed to establish toxicity and efficacy of these compounds. The routes, being short and direct, should also allow for future large-scale kg production to facilitate human testing and commercialization.

A series of F4-4 analogs were synthesized with variations in the Diels-Alder starting materials as shown in Scheme 3, using synthetic routes similar to Schemes 1 and 2. Various other starting materials for the Diels-Alder reaction can be used as well. Some of these starting materials are commercially available. Others can be synthesized using known synthetic techniques. These analogs and their biological activities are shown in Scheme 4 below. The corresponding synthetic intermediates and their biological activities are shown in Scheme 5 below. Several late stage F4-4 analogs and their biological activities are shown in Scheme 6 below -continued
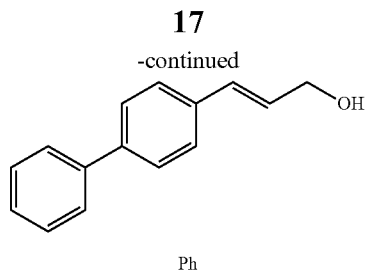
Ph
Scheme 4, Scaphopetalone Analogs And Their Biological Activities
A same series
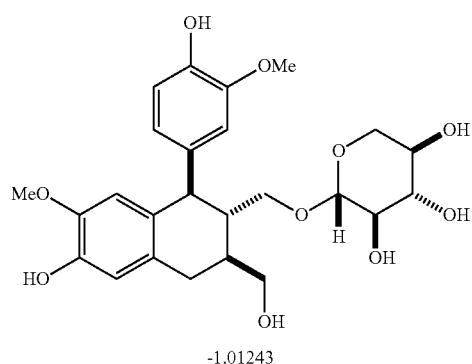
-1.01243
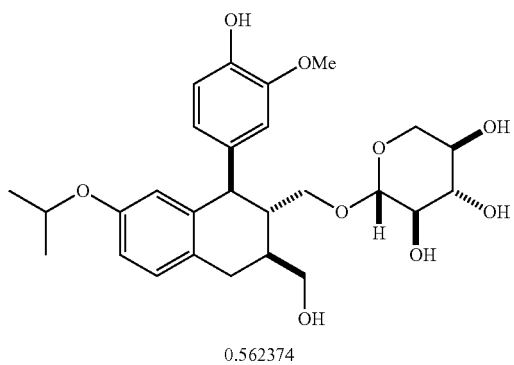
0.562374
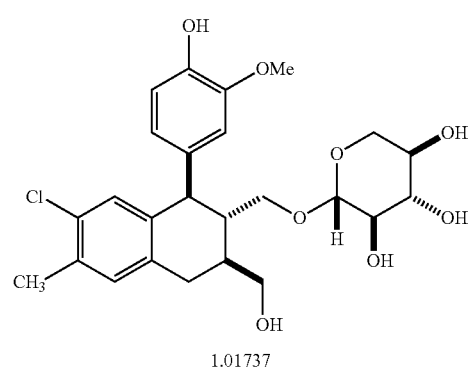
1.01737
-continued
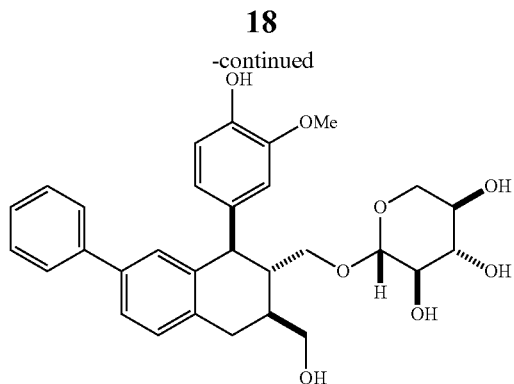
1.69337
MeO, t-Bu series
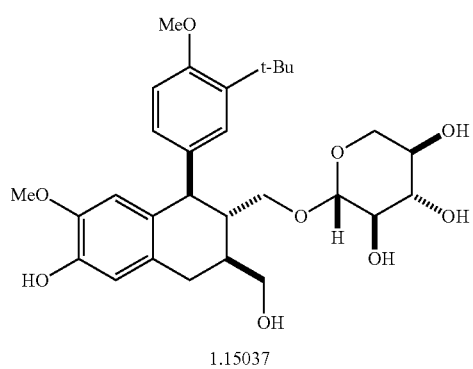
1.15037
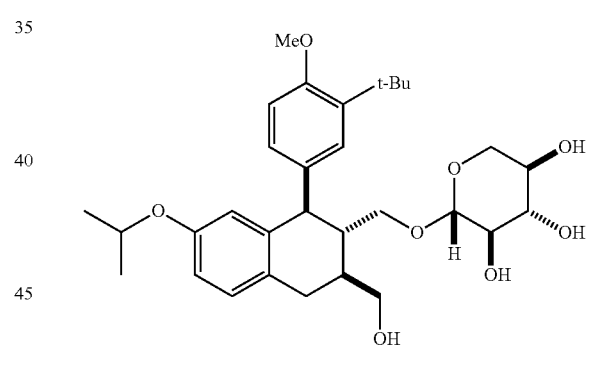
2.72517
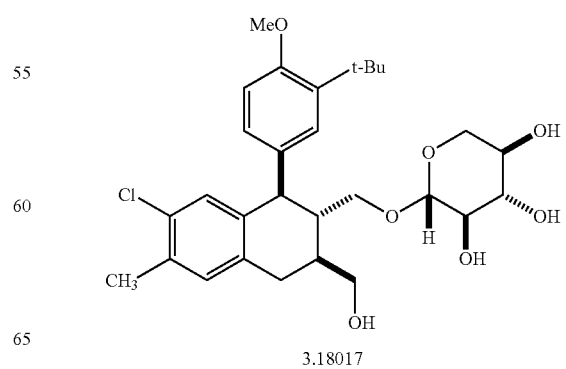
3.18017

-continued
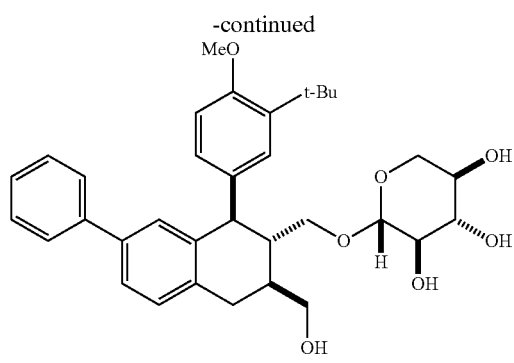
3.85617
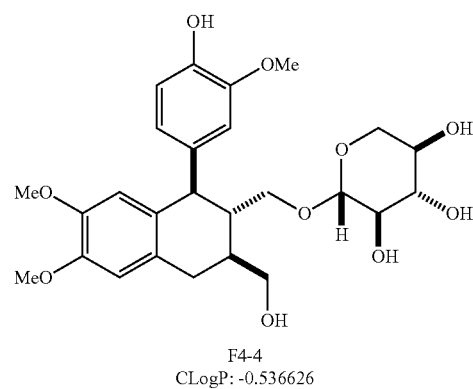
F4-4
CLogP: -0.536626
MethAcetal series
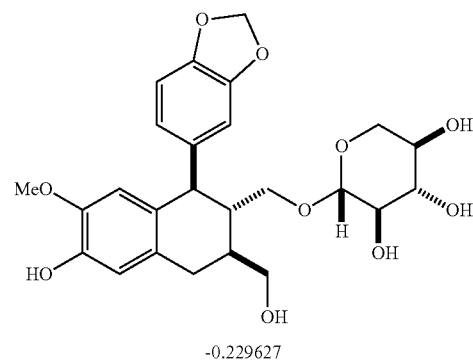
-0.229627
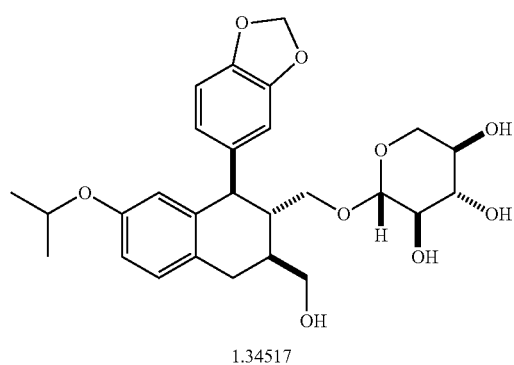
1.34517
-continued
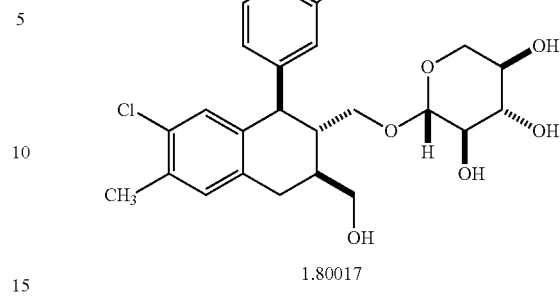
1.80017
2.47617
F, MeO series
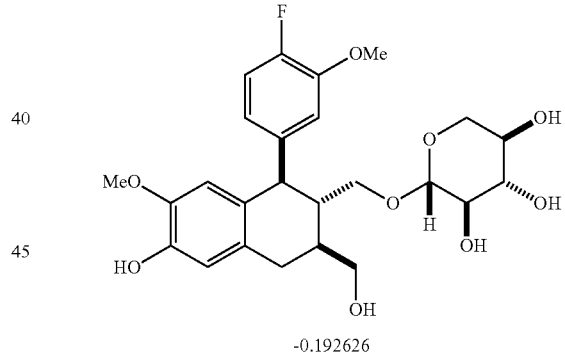
-0.192626
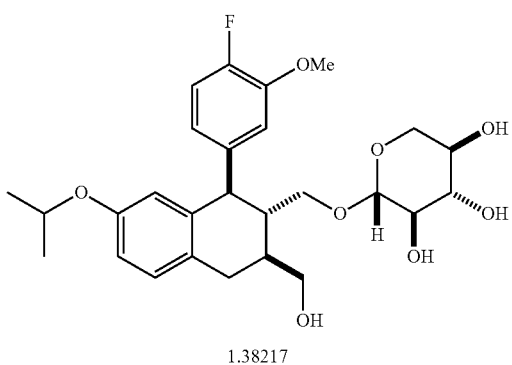
1.38217

-continued
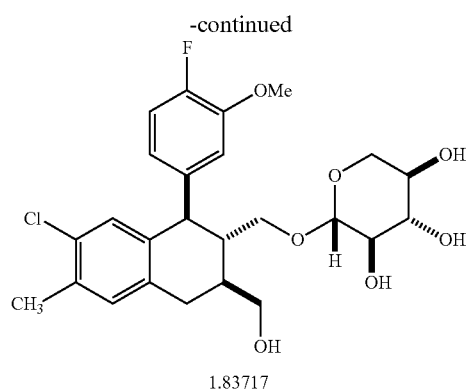
1.83717
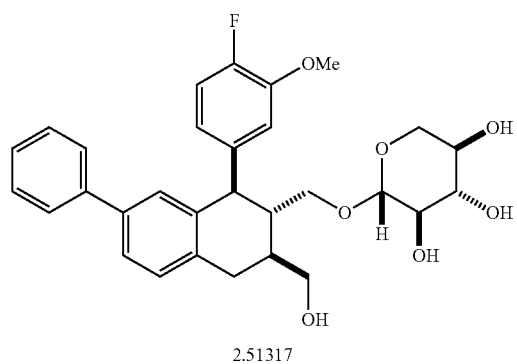
2.51317
B same series
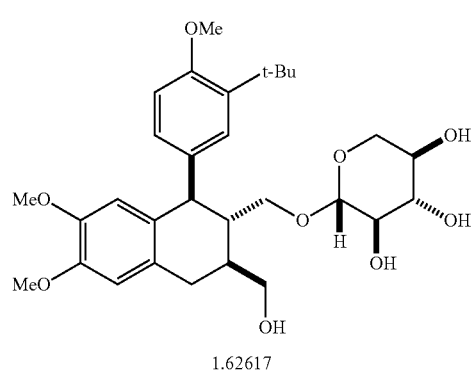
1.62617
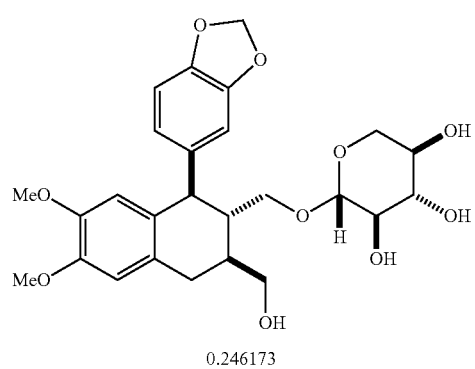
0.246173
-continued
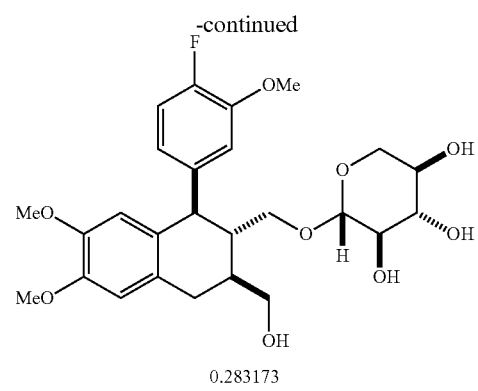
0.283173
Scheme 5, Scaphopetalone Intermediates And Their Biological Activities
A same series
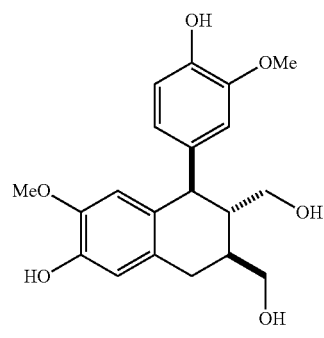
0.7004
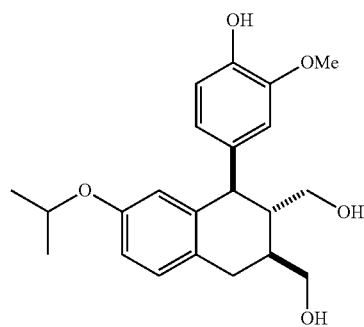
2.2752
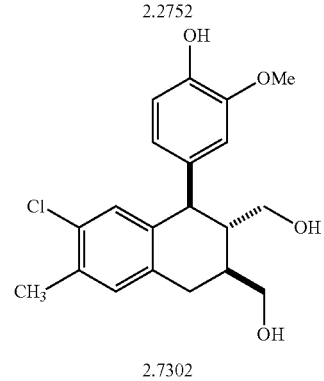
2.7302

-continued
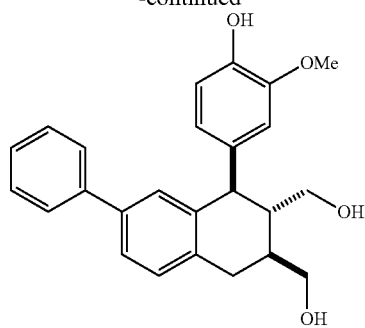
3.4062
MeO, t-Bu series
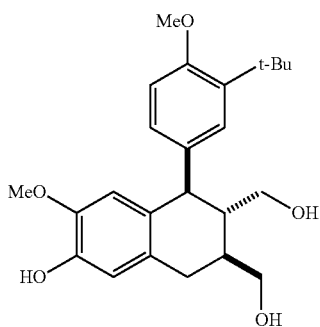
2.8632
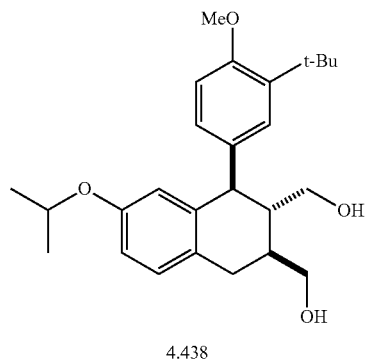
4.438
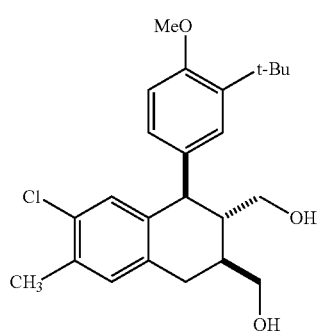
4.893
-continued
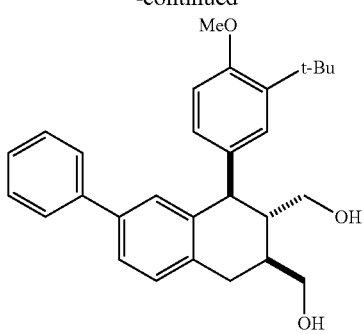
5.569
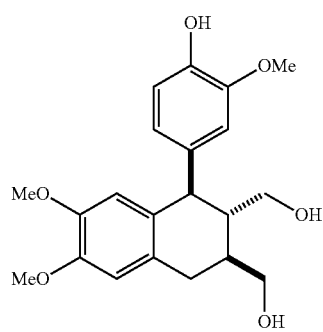
aglycone
F4-4 de-glyco
CLogP: 1.1762
MethAcetal series
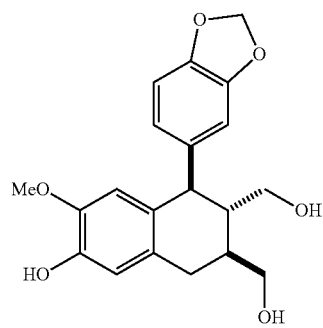
1.4832
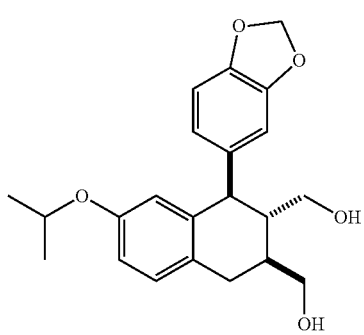
3.058

25
-continued
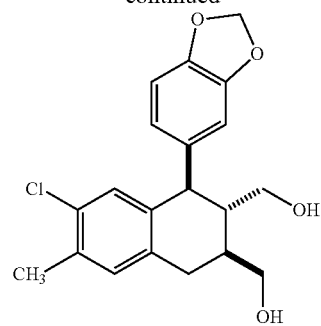
3.513
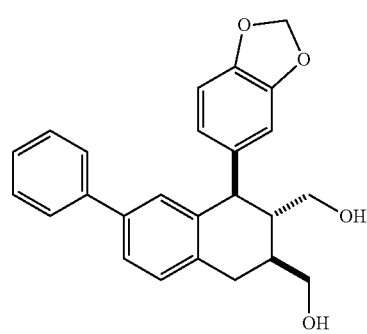
4.189
F, MeO series
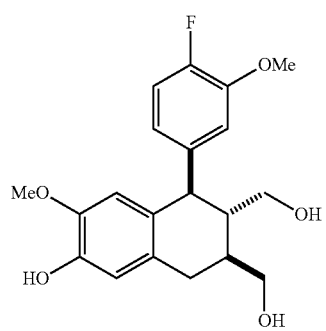
1.5202
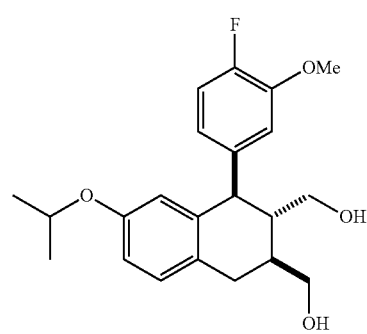
3.095
26
-continued
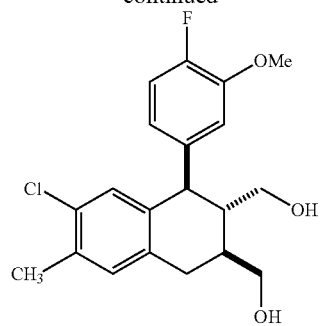
3.55
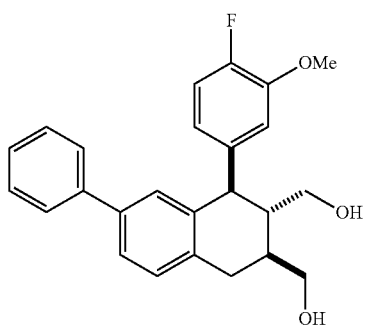
4.226
B same series
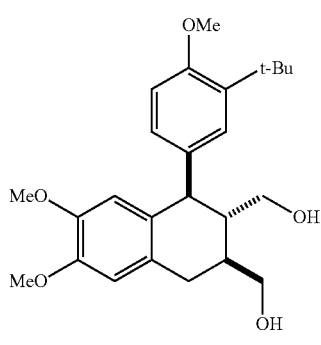
3.339
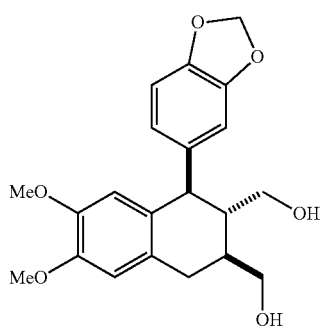
1.959

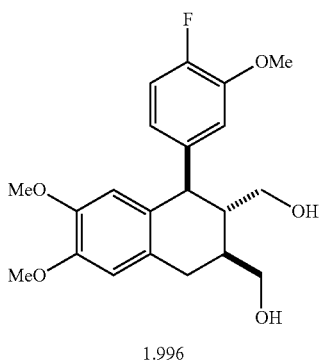

1.996

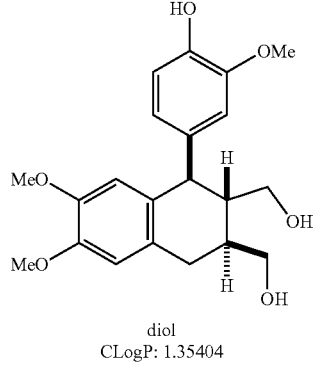

diol
CLogP: 1.35404

Scheme 6, Scaphopetalone Late Stage Analogs And Their Biological Activities

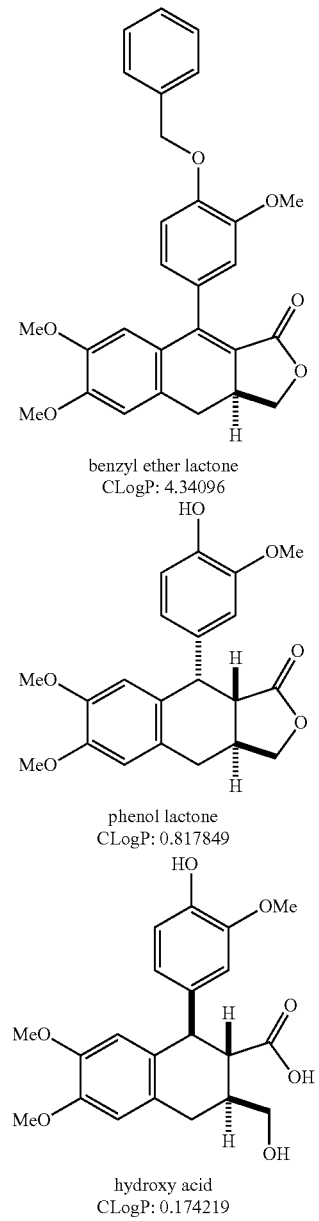

benzyl ether lactone
CLogP: 4.34096 phenol lactone
CLogP: 0.817849 hydroxy acid
CLogP: 0.174219

Examples

Extraction Method

Approximately 100 g root tissue are freeze dried, ground with a Wiley Mill, covered with hexane, and after 1 hour the stirred mixture is filtered in double layers of cheesecloth. Hexane removes waxes and other inactive compounds and is discarded. The resulting tissue is covered with acetone, mixed, filtered, and the supernatant collected. The acetone is removed and 50 mL of distilled water is added to the dried extract. This is vortexed to homogenize the extract, filtered through 0.2 μm Minisart filter (Sartoirus Stedim Biotech, France), placed in 1.5 mL Ependorf tubes, and stored at −20° C. until assayed against the viruses.

Detection of Anti-Viral Activity by Mini-Plaque Reduction Bioassay

Details of this bioassay are outlined in Jaeger Greer et al., Activity Of Acetone And Methanol Extracts From Thirty-One Medicinal Plant Species Against Herpes Simplex Virus Types 1 And 2, Pharmaceutical Biology, 2010, 48 (9), pp. 1031-1037, which is incorporated by reference herein. Briefly Vero African Green Monkey Kidney C1008 cells are grown to form a monolayer with near 99% confluency in media in cell culture plates. Following the natural order of infection, HSV-2 in a predetermined amount is added to cells growing in the media. Then predetermined concentrations of the plant extract and/or compounds are added. Plates are incubated at 36° C. overnight and antiviral activity of the extract or compound against the virus is measured by counting the number of single infected cells ('miniplaques') and number of small plaques (multiple infected, disrupted cells). These plaques could be determined microscopically because cells are exposed to FAA fixative and then immunoperoxidase stain which has an antibody that reacts (stains) to viral protein (FIG. 2). Antiviral activity of test drugs are detected in cells exposed to the drug by assessing inhibition of viral protein synthesis (virus replication) as measured by reduction in number of miniplaques when compared to the controls without the drug. HSV-1 and H. zoster have been tested in the same way and show similar inhibition by the drug. Possible drug toxicity to cells is assessed by microscopic observation of cytologic changes and cell multiplication rates.

Sensitivity of Vaccinia Virus to K. pinnata Extract

Cell sheets were grown to ~95% confluency. The growth media were decanted; cells washed with fresh media; and 1 mL fresh medium was added per well. Dilutions of drug were added to appropriate wells in 100 uL aliquots. After 30 minutes, 0.1 mL of working virus dilution was added to the appropriate wells, mixed thoroughly, and incubated at 36° C. Appearance of primary plaques was observed under a microscope. At 2 days post-infection, cultures were fixed in FAA fixative for 1 hour, and then washed and stained with crystal violet. Plaques were counted on an inverted microscope. The plaques in the virus controls were assessed as large plaques, and the plaques in the drug-treated wells were small plaques. Preliminary data showed that vaccinia virus replication was inhibited by material in the *K. pinnata* extract. The results were shown in the table below. Cells: Vero cell subline C1008, Passage 20. Medium: Dulbecco's Modified Eagle Medium, +gentamycin, +HEPES buffer, +5% Cosmic calf serum. Virus: Vaccinia virus, BYU Lot Y3358 @ $10^{-3}$ dilution (Est. ~$10^2$ PFUs/0.1 ml). Drug: K.p. extract (September 10 batch). Plastic: 24 well plates (Corning).

TABLE 1

Sensitivity of Vaccinia Virus to K.p. Extract

| Cell/drug toxicity Control[1] | [Drug][2] | No. Plaques/ well[3] | Mean # Plaques[4] | Virus Controls[5] |
|---|---|---|---|---|
| Slight toxicity on very few cells | 1:20 | 0, 0 | 0 (100%) | 69, 67, 68, 73 |
| No toxicity | 1:40 | 0, 0 | 0 (100%) | (mean control plaques = 69) |
| No toxicity | 1:80 | 5, 1 | 3 (96%) | |
| No toxicity | 1:160 | 25, 24 | 25 (64%) | |

[1]Assessed by cell detachment and morphological changes.
[2]Final drug concentration in the culture wells.
[3]Number of plaques formed in each of duplicate wells.
[4]Mean number of plaques in the wells followed by (% of inhibition compared to virus control plaques formed in the absence of drug. This assay did not go out to the EC50 endpoint).
[5]There were four replicate control cultures (wells).

Experimentals (E)-Methyl 3-(3,4-dimethoxyphenyl)acrylate

To a stirred flask containing methanol (0.2 M, 190 mL) was added 3-(3,4-dimethoxyphenyl)acrylic acid (8.0 g, 38.4 mmol) followed by sulfuric acid (10 mol %, 0.21 mL, 0.38 g,). The mixture was heated at reflux (65° C.) for 12 hr. The mixture was cooled to rt and saturated NaHCO$_3$ was slowly added (20 mL). The solution was added to a separatory funnel containing brine (50 mL, sat. NaCl). The aqueous layer was extracted with methylene chloride (3×30 mL). The combined organic layers were dried (MgSO$_4$), concentrated, and submitted to silica gel chromatography (4:1, hexanes/ethyl acetate) to access the desired methyl ester (8.1 g, 95%) as a colorless oil: R$_f$ 0.25 (20% EtOAc/hexanes), $^1$H NMR (300 MHz, CDCl$_3$) δ 7.65 (d, 1H, J=20 Hz), 7.10 (m, 2H), 6.88 (d, 1H, 4 Hz), 6.34 (d, 1H, 20 Hz), 3.91 (s, 6H), 3.80 (s, 3H), IR (cm$^{-1}$) 3065, 2944, 1695.

(E)-3-(3,4-Dimethoxyphenyl)prop-2-en-1-ol

To a stirred solution of (E)-methyl 3-(3,4-dimethoxyphenyl)acrylate (5.0 g, 22.5 mmol) in methylene chloride (0.1 M, 225 mL) cooled to 0° C. (ice water bath) under Ar gas was slowly added DIBAL (diisobutylaluminum hydride, 56 mL, 1.0 M in heptane, 2.5 equiv) via syringe (5 min). The mixture was allowed to warm to rt (2 hr). To the mixture was slowly added methanol (20 mL) followed by aqueous HCl (1 M, 2 mL). The mixture was added to a separatory funnel containing water (40 mL). The aqueous layer was extracted with methylene chloride (2×30 mL) and the combined organic layers were dried (MgSO$_4$). The dry organic layers were submitted to silica gel chromatography (50% EtOAc/hexanes) to obtain the desired alcohol (98%, 4.2 g) as a colorless oil: R$_f$ 0.05 (20% EtOAc/hexanes), $^1$H NMR (300 MHz, CDCl$_3$) δ 6.97 (m, 2H), 6.83 (m, 1H), 6.58 (d, 1H, J=20 Hz), 6.22 (dt, J=20, 7 Hz, 1H), 4.30 (d, J=7 Hz, 2H), 3.88 (s, 3H), 3.86 (s, 3H), IR (cm$^{-1}$) 3490, 2934.

1-(Benzyloxy)-4-(2,2-dibromoethene)-2-methoxybenzene

To a solution of triphenylphosphine (3 equiv, 61.8 mmol, 16.2 g) in methylene chloride (0.2 M, 100 mL) cooled to 0° C. under argon gas, was added carbon tetrabromide (1.5 equiv, 30.9 mmol, 10.24 g) and stirring continued for 15 min. To the solution was added 4-(benzyloxy)-3-methoxybenzaldehyde (5 g, 20.6 mmol) in methylene chloride (2 M, 11 mL). The resultant mixture was stirred at rt for 15 hr. The mixture was concentrated and triturated with cold hexanes (60 mL) and filtered (paper cone) to remove excess triphenylphosphine. The filtrate was concentrated and subjected to silica gel chromatography (10% EtOAc/hexanes) to obtain the dibromoolefin product (80%, 6.2 g) as a yellow solid: Rf 0.80 (20% EtOAc/hexanes), $^1$H NMR (300 MHz, CDCl$_3$) δ 7.40 (m, 5H), 7.33 (m, 1H), 7.22 (s, 1H), 7.02 (d, J=4 Hz, 1H), 6.83 (d, J=4 Hz, 1H), 5.18 (s, 2H), 3.94 (s, 3H).

3-(4-(Benzyloxy)-3-methoxyphenyl)propiolic Acid

To a dry THF (0.2 M, 63 mL) solution containing 1-(benzyloxy)-4-(2,2-dibromoethene)-2-methoxybenzene (12.6 mmol, 5 g) under Ar gas cooled to −78° C. (dry ice/acetone bath) was added a solution of n-butyllithium (0.6 M, 1.9 equiv, THF, 23.9 mmol, 40 mL). The yellow-green solution was stirred 20 min at −78° C. and solid carbon dioxide (crushed, 10 equiv, 126 mmol, 6 g) was added at once. The mixture was allowed to warm to rt and stirring continued for 3 hr. The mixture was added to a separatory funnel containing ethyl acetate/hexanes (50 mL, 50%) and 1 M HCl (10 mL). The organic layer was extracted with ethyl acetate (3×20 mL). The combined organic layers were dried (MgSO$_4$), concentrated to subjected to silica gel chromatography (50% EtOAc/hexanes) to access the desired propiolic acid (82%, 2.9 g): R$_f$ 0.2 (35% EtOAc/hexanes), $^1$H NMR (300 MHz, CDCl$_3$) δ 7.40 (m, 5H), 7.20 (m, 1H), 7.17 (m, 1H), 6.89 (d, J=5 Hz, 1H), 5.21 (s, 2H), 3.91 (s, 3H).

(E)-3-(3,4-Dimethoxyphenyl)allyl 3-(4-(benzyloxy)-3-methoxyphenyl)propiolate

To a toluene solution (0.1 M, 51 mL) with (E)-3-(3,4-dimethoxyphenyl)prop-2-en-1-ol (1.0 equiv, 5.15 mmol, 1.0 g) at 0° C. was added 3-(4-(benzyloxy)-3-methoxyphenyl) propiolic acid (1.7 equiv, 8.76 mmol, 2.5 g), followed by DMAP (4-N,N-dimethylaminopyridine, 0.2 equiv, 1.03 mmol, 0.13 g) and DCC (N,N-dicyclohexylcarbodiimide, 2.5 equiv, 12.9 mmol, 2.66 g). The mixture was stirred at 0° C. for 2 hr. The mixture was warmed to rt and filtered through silica gel (20 g, hexanes) to remove the urea by-product. The filtrate was concentrated and subjected to silica gel chromatography (15% EtOAc/hexanes) to yield the desired ester as a yellow solid (78%, 1.84 g): R$_f$ 0.3 (25% EtOAc/hexanes), $^1$H NMR (500 MHz, CDCl$_3$) δ 7.4 (m, 5H), 7.16 (d, J=4 Hz, 1H), 7.1 (s, 1H), 6.96 (m, 2H), 6.83 (m, 2H), 6.67 (d, J=20 Hz, 1H), 6.22 (dt, J=20, 6 Hz), 5.19 (s, 2H), 4.87 (d, J=6 Hz, 2H), 3.90 (s, 3H), 3.88 (s, 3H), 3.86 (s, 3H).

(dl)-9-(4-(Benzyloxy)-3-methoxyphenyl)-6,7-dimethoxy-3a,4-dihydronaphtho[2,3-c]furan-1(3H)-one To a solution of (E)-3-(3,4-dimethoxyphenyl)allyl 3-(4-(benzyloxy)-3-methoxyphenyl)propiolate (1 equiv, 0.10 g, 0.218 mmol) in benzonitrile (0.1 M, 2.2 mL) was added 2,6-di-t-butylhydroxytoluene (BHT, 0.2 equiv, 0.044 mmol, 10 mg). The mixture was heated at reflux for 6 hr. The mixture was cooled to rt, concentrated, and subjected to silica gel chromatography (50% EtOAc/hexanes) to yield the desired Diels-Alder product (65%, 65 mg): Rf 0.1 (25% EtOAc/hexanes), $^1$H NMR (500 MHz, CDCl$_3$) δ 7.49 (m, 2H), 7.39 (m, 2H), 7.33 (m, 1H), 6.97 (d, J=4 Hz, 1H), 6.90 (m, 1H), 6.88 (d, J=4 Hz, 1H), 6.80 (s, 1H), 6.54 (s, 1H), 5.20 (s, 2H), 4.71 (dd, J=7.0, 7.0 Hz, 1H), 4.02 (dd, J=7.0, 7.0 Hz, 1H), 3.93 (s, 3H), 3.88 (s, 3H), 3.63 (s, 3H), 3.42 (m, 1H), 2.95 (dd, J=12, 4 Hz, 1H), 2.82 (dd, J=12, 10 Hz, 1H), IR (cm$^{-1}$) 2936, 1742, 1511.

The invention claimed is:

1. A compound or a pharmaceutically acceptable salt thereof, which is

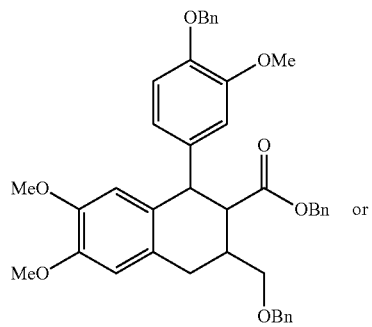

or

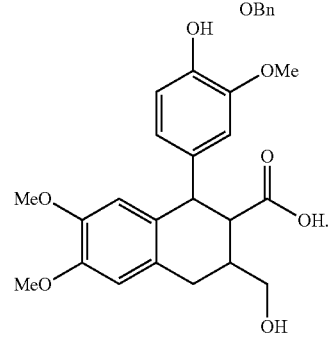

2. A compound or a pharmaceutically acceptable salt thereof selected from the group consisting of:

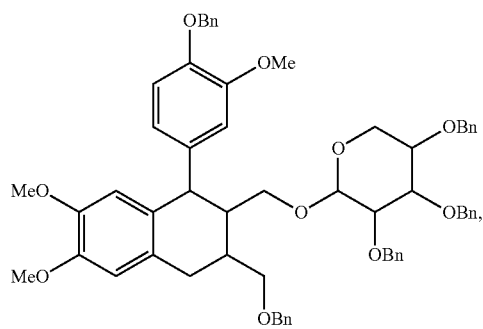

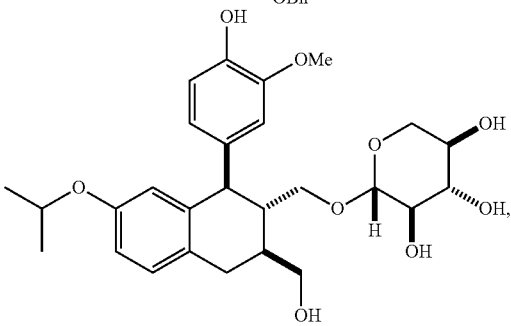

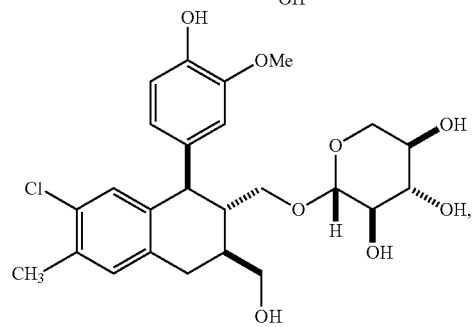

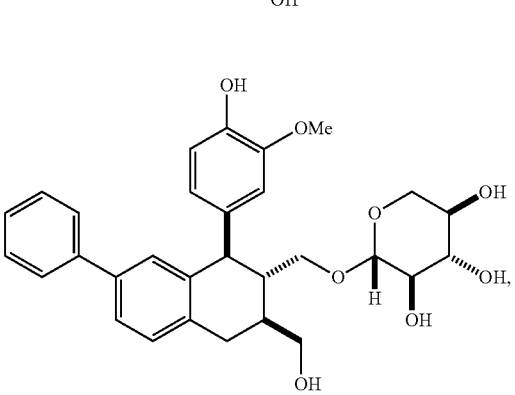

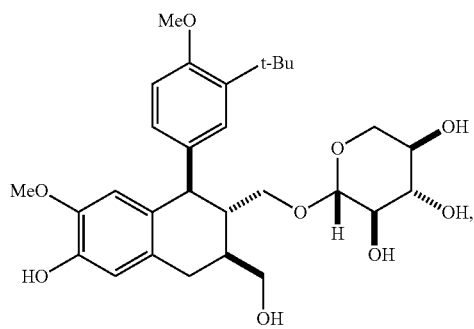

33
-continued
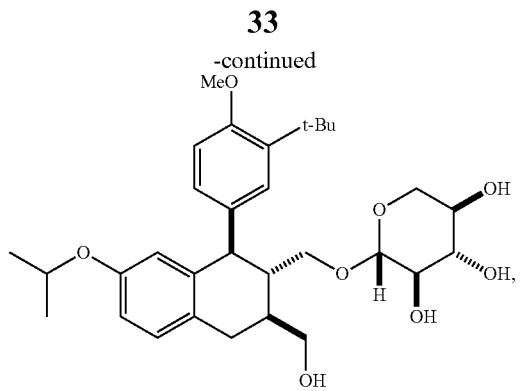
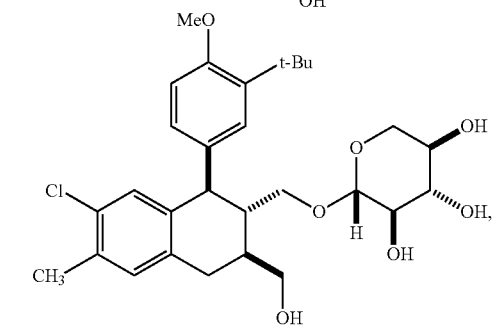
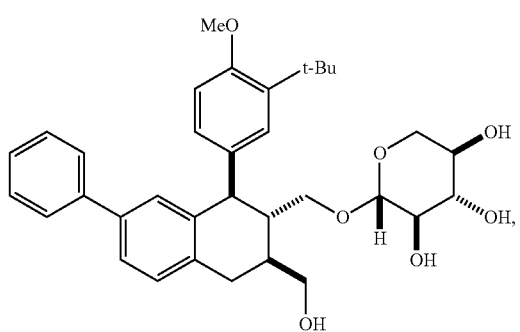
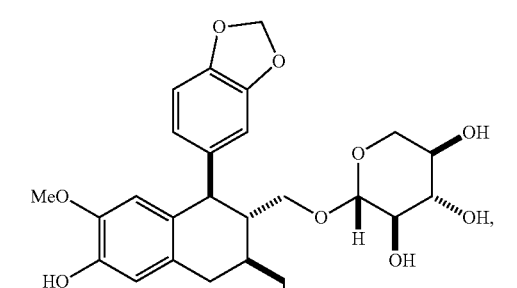
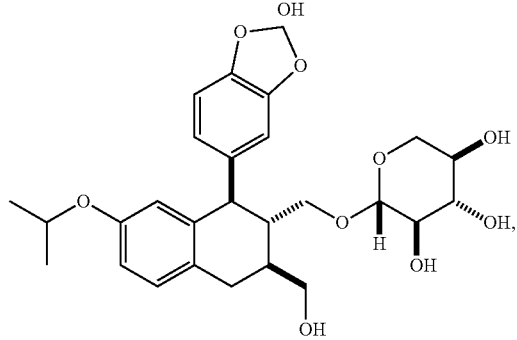
34
-continued
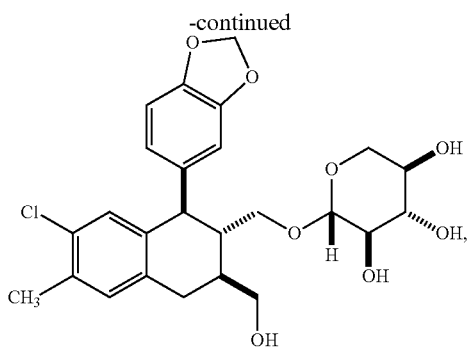
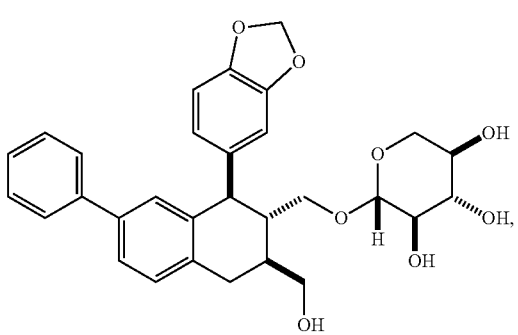
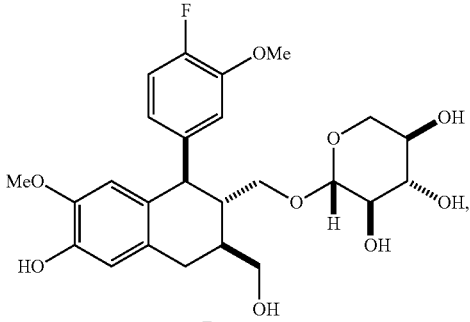
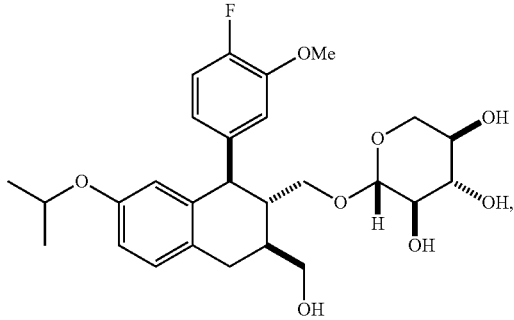
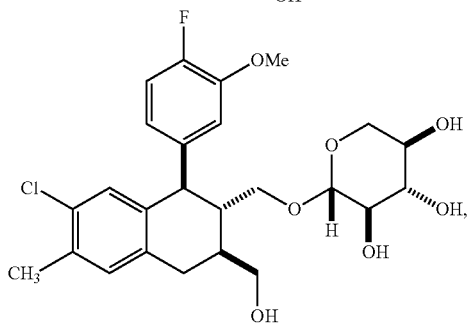

35
-continued
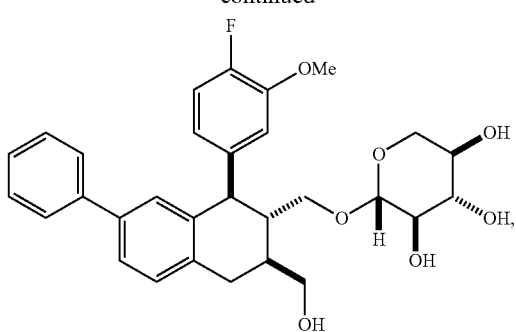
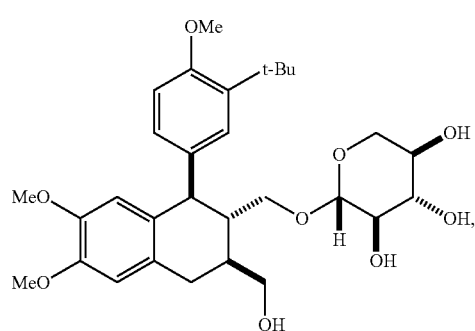
36
-continued
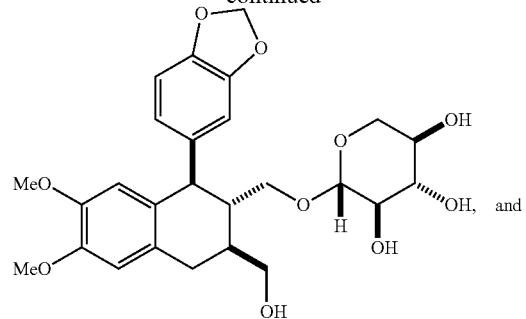
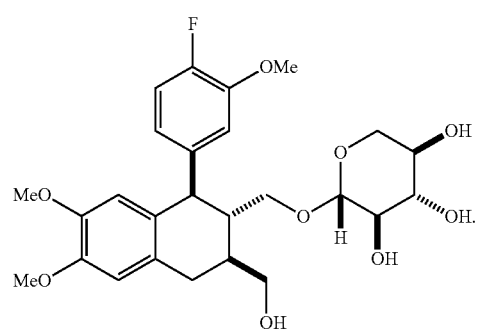
* * * * *